United States Patent [19]
Prusiner et al.

[11] Patent Number: 6,008,435
[45] Date of Patent: *Dec. 28, 1999

[54] DETECTING COW, SHEEP AND HUMAN PRIONS IN A SAMPLE AND TRANSGENIC MICE USED FOR SAME

[75] Inventors: Stanley B. Prusiner; Michael R. Scott; Glenn C. Telling, all of San Francisco, Calif.

[73] Assignee: The Regents of the University of California, Oakland, Calif.

[*] Notice: This patent is subject to a terminal disclaimer.

[21] Appl. No.: 08/935,363

[22] Filed: Sep. 22, 1997

Related U.S. Application Data

[63] Continuation-in-part of application No. 08/692,892, Jul. 30, 1996, Pat. No. 5,792,901, which is a continuation-in-part of application No. 08/521,992, Aug. 31, 1995, Pat. No. 5,908,969, which is a continuation-in-part of application No. 08/509,261, Jul. 31, 1995, Pat. No. 5,763,740, which is a continuation-in-part of application No. 08/242,188, May 13, 1994, Pat. No. 5,565,186.

[51] Int. Cl.$^6$ ................................................. C12N 15/00
[52] U.S. Cl. ................................... 800/18; 800/3; 800/9; 424/9.1; 424/9.2; 435/7.21
[58] Field of Search ..................................... 800/3, 13, 14, 800/15, 16, 17, 18, 21, 22, 25

[56] References Cited

U.S. PATENT DOCUMENTS 5,763,740  6/1998  Prusiner et al. ............................. 800/3
5,792,901  11/1998  Prusiner et al. ............................. 800/3

FOREIGN PATENT DOCUMENTS

WO 91/19810  12/1991  WIPO.
WO 93/10227  5/1995  WIPO.

OTHER PUBLICATIONS

Hammer et al. Spontaneous inflammatory disease in transgenic rats expressing HLA–B27 and human b2m: An animal model of HLA–B27–associated human disorders. Cell 63: 1099–1112, Nov. 1990.

Wall, RJ Transgenic livestock: Progress and prospects for the future. Theriogenology 45:57–68, 1996.

Martin et al. Direct sequencing of PCR amplifed pig PrP genes. Biochimica et Biophysica Acta 1270(2–3): 211–214, 1995.

Prusiner, S.B. "Molecular Biology of Prions Causing Infectious and Genetic Encephalopathies of Humans as well as Scrapie of Sheep and BSE of Cattle." *Develop. Biol. Standard.* (1991) vol. 75, pp. 55–74, especially p. 65.

Telling, G.C. et al. "Prion Propagation in Mice Expressing Human and Chimeric PrP Transgenes Implicates the Interaction of Cellular PrP with Another Protein." *Cell* Oct. 6, 1995, vol. 83, pp. 79–90, especially p. 84.

Baker, H.F., et al. "Aminoacid Polymorphism in Human Prion Protein and Age at Death in Inherited Prion Disease," *Lancet* (1991) 337:1286.

Barry, R.A., et al., "Monoclonal Antibodies to the Cellular and Scrapie Prion Proteins," *J. Infect. Dis.* (1986) 154(3):518–521.

Basler et al., "Scrapie and Cellular PrP Isoforms Are Encoded by the Same Chromosomal Gene," *Cell*, (1986) 46:417–28.

Berger, J.R., et al., "Creutzfeldt–Jakob disease in a physician: A review of the disorder in health care workers", *Neurology*, (1993) 43:205–206.

Bolton et al., "Identification of a Protein That Purifies with the Scrapie Prion," *Science* (1982) 218: 1309–11.

Brown et al., "Friendly Fire in Medicine: Hormones, Homografts, and Cruetzfeldt–Jakob Disease," *Lancet* (1992) 340: 24–27.

Buchanan et al., "Mortality, Neoplasia, and Creutzfeld–Jakob Disease in Patients Treated with Human Pituitary Growth Hormone in the United Kingdom", *BMJ* (1991) 302:824–828.

Bueler et al., "Mice Devoid of PrP are Resistant to Scrapie," *Cell* (1993) 73:1339–1347.

Bueler et al., "Normal Development and Behavior of Mice Lacking the Neuronal Cell–surface PrP Protein," *Nature* (1992) 356:577–582.

Carlson et al., "Linkage of Protein and Scrapie Incubation Time Genes," *Cell* (1986) 46:503–511.

Chandler, "Encephaolpathy in Mice Produced by Inoculation with Scrapie Brain Material," Lancet (1961) 1:1378–79.

Cochius et al, "Creutzfeldt–Jakob Disease in a Recipient of Human Pituitary–Derived Gonadotrophin: A Second Case," *J. Neurol. Neurosurg. Psychiatry* (1992) 55:1094–1095.

Cochius et al., "Creutzfeldt–Jakob Disease in a Recipient of Human Pituitary–Derived Gonadotrophin," *Aust. N.Z. J. Med.* (1990) 20:592–593.

Collinge et al., "Genetic Predisposition to Latrogenic Creutzfeldt–Jakob Disease," *Lancet* (1991) 337:1441–1442.

Cousens, S.N., et al., "Geographical distribution of cases of Creutzfeldt–Jakob disease in England and Wales 1970–84", *J. Neurol. Neurosurg. Psychiatry* (1990) 53:459–465.

(List continued on next page.)

*Primary Examiner*—Bruce R. Campell
*Assistant Examiner*—Anne-Marie Baker
*Attorney, Agent, or Firm*—Bozicevic, Field & Francis LLP

[57] ABSTRACT

Transgenic animals are produced which animals have (1) their endogenous PrP gene ablated; and (2) have an exogenous PrP gene from a genetically diverse animal. The transgenic animal is preferably a mouse, rat or hamster with mice being particularly preferred. The exogenous PrP gene is preferably from a sheep, cow, or pig with cow PrP genes being particularly preferred. When a mouse of the invention is inoculated with a sample containing prions which generally only infects a genetically diverse species (e.g. a cow) the mouse will become ill within about 250 days or less. Methods of producing the transgenic animals are disclosed including (1) microinjecting a mouse egg (having an ablated endogenous PrP gene) with a bovine PrP gene, or (2) breeding a mouse with an ablated PrP gene with a mouse with a bovine PrP gene. Mice produced are used to test samples for the presence of prions which generally only infect cows.

10 Claims, No Drawings

OTHER PUBLICATIONS

Farlie, P.G., et al., "bcl–2 Transgene expression can protect neurons against developmental and induced cell death", *Proc. Natl. Acad. Sci. USA* (1995) 92:4397–4401.

Gabriel et al., "Molecular Cloning of a Candidate Chicken Prion Protein," *Proc. Natl. Acad. Sci. USA* (1992) 89:9097–9101.

Gajdusek, D.C., "Unconventional Viruses and the Origin and Disappearance of Kuru," *Science* (1977) 197:943–960.

Gibbs, Jr. et al., "Creutzfeldt–Jakob Disease Infectivity of Growth Hormone Derived from Human Pituitary Glands," *N.Engl. J. Med.* (1993) 328:358–359.

Goldfarb et al, "Fatal Familial Insomnia and Familial Creutzfeldt–Jakob Disease: Disease Phenotype Determined by a DNA Polymorphism," *Science* (1992) 258:806–808.

Goldman et al., "Two Alleles of a Neural Protein Gene Linked to Scrapie in Sheep," *Proc. Natl. Acad. Sci. USA* (1990) 87:2476–2480.

Goldmann et al., "Different Forms of the Bovine PrP Gene Have Five of Six Copies of a Short, G–C Rich Element within the protein–coding Exon," *J. Gen. Virol.* (1991) 72:201–204.

Harris et al., "A Prion–like Protein from Chicken Brain Copurifies with an Acetylcholine Receptor–Inducing Activity," *Proc. Natl. Acad. Sci. USA* (1991) 88:7664–7668.

Hasty, P., et al., "Introduction of a subtle mutation into the Hox–2.6 locus in embryonic stem cells", *Nature* (1991) 350:243–246.

Healy et al., "Creutzfeldt–Jakob Disease After Pituitary Gonadotrophins: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Hsaio et al.,"Linkage of a Prion Protein Missense Variant to Gerstmann–Straussler Syndrome," *Nature* (1989) 383:342–345.

Hsaio et al., "A Prion Protein Variant in a Family with the Telencephalic Form of Gerstmann–Strussler–Scheinker Syndrome," *Neurology* (1991) 41:681–684.

Hsaio et al., "Inherited Human Prion Disease," *Neurology* (1990) 40:1820–1827.

Kascsak, R.J., et al., "Mouse Polyclonal and Monoclonal Antibody to Scrapie–Associated Fibril Proteins," *J. Virol.* (1987) 61(12):3688–3693.

Koch et al.,"Creutzfeldt–Jakob Disease in a Young Adult with Idiopathic Hypopituitarism," *N. Engl. J. Med.* (1985) 313:731–733.

Kretzchmar et al., "Molecular Cloning of a Human Prion Protein cDNA," *DNA* (1986) 5:315–324.

Kretzchmar et al., "Molecular Cloning of a Mink Prion Protein Gene," *J.Gen.Virol.* (1992) 73:2757–2761.

Lasmezas et al.,"Recombinant Human Growth Hormone and Insulin–Like Growth Factor I Induce PRP Gene Expression in PC12 Cell," *Biochem. Biophys. Res.Commun.* (1993) 196:1163–1169.

Locht et al.,"Molecular Cloning and Complete Sequence of Prion Protein cDNA from Mouse Brain Infected with the Scrapie Agent," *Proc. Natl. Acad. Sci USA* (1986) 83:6372–6376.

Manuelidis et al., "Serial Propagation of Creutzfeldt–Jakob Disease in Guinea Pigs," *Proc. Natl. Acad. Sci. USA* (1976) 73:223–227.

Manuelidis et al., "Interspecies Transmission of Creutzfeldt– Jakob Disease to Syrian Hamsters with Reference to Clinical Syndromes and Strain of Agent," *Proc. Natl. Acad. Sci USA* (1978) 75:3432–3436.

McKinley et al, "A Protease–Resistant Protein is a Structural Component of the Scrapie Prion," *Cell* (1983) 35:57–62.

Medori et al., "Fatal Familial Insomnia, a Prion Disease with a Mutation at Codon 178 of the Prion Protein Gene," *N .Engl.J. Med.* (1992) 326:444–449.

Muramoto, T., et al., "The Sequential Development of Abnormal Prion Protein Accumulation in Mice with Creuzfeldt–Jakob Disease," *Am. J. Pathol.* (1992) 140(6):1411–1420.

Nisbet et al., "Creutzfeldt–Jakob Disease in a Second Patient Who Received a Cadaveric Dura mater Graft," *J.Am. Med.Assoc.* (1989) 261:1118.

Palmer, M.S., et al., "Homozygous Prion Protein Genotype Predisposes to Sporadic Creutzfeldt–Jakob Disease", *Nature* (1991) 352:340–342.

Patel, "France Reels at Latest Medical Scandal," *New Scientist*, Jul. 31, 1993, p. 4.

Patel, "Placenta Donors to be Screened for Brain Disease," *New Scientist*, Nov. 20, 1993, p. 10.

Pan, K.M., et al., "Conversion of β–sheets features in the formation of the scrapie prion proteins", *Proc. Natl. Acad. Sci. USA* (1993) 90:10962–10966.

Prusiner et al., "Measurement of the Scrapie Agent Using an Incubation Time Interval Assay," *Annals Neurol.* (1982) 11(4):353–358.

Prusiner et al., "Further Purification and Characterization of Scrapie Prions," *Biochemistry* (1982) 21:6942–50.

Prusiner, S.B., et al., "Scrapie Prions Aggregate to Form Amyloid–like Birefringent Rods,"0 *Cell* (1983) 35:349–358.

Prusiner et al., "Transgenic Studies Implicate Interactions Between Homologous PrP Isoforms in Scrapie Prion Replication," *Cell* (1990) 63:673–686.

Prusiner et al., "Molecular Biology of Prion Diseases," *Science* (1991) 252:1515–1522.

Prusiner et al., "Ablation of the Prion Protein (PrP) Gene in Mice Prevents Scrapie and Facilitates Production of Anti–PrP Antibodies," *Proc. Natl. Acad. Sci. USA* (1993) 90:10608–10612.

Prusiner, S.B., et al., "Immunologic and Molecular Biological Studies of Prion Proteins in Bovine Spongiform Encephalopathy," *J. Infect. Dis.* (1993) 167:602–613.

Prusiner et al., "Prion Diseases and Neurodegeneration," *Ann.Rev.Neurosci.* (1994) 17:311–339.

Raeber et al., "Attempts to Convert the Cellular Prion Protein into the Scrapie Isoform in Cell–Free Systems," *J. Virol.* (1992) 66:6155–6163.

Ridley et al., *Lancet* Occupational Risk of Creuzfeldt–Jakob Disease, (1993) 341:641–2.

Rogers, M. et al., "Epitope Mapping of the Syrian Hamster Prion Protein Utilizing Chimeric and Mutant Genes in a Vaccinia Virus Expression System," *J. Immunol.* (1991) 147(10):3568–3574.

Scott, M., et al., "Transgenic Mice Expressing Hamster Prion Protein Produce Species–Specific Infectivity and Amyloid Plaques," *Cell* (1989) 59:847–857.

Scott et al, "Chimeric Prion Protein Expression in Cultured Cells and Transgenic Mice," *Protein Sci.* (1992) 1:986–97.

Scott et al, "Propagation of Prions with Artificial Properties in Transgenic Mice Expressing Chimeric PrP Genes," *Cell* (1993) 73:979–988.

Serban, D., et al. "Rapid detection of Creutzfeldt–Jakob disease and scrapie prion proteins", *Neurology* (1990) 40:110–117.

Stahl et al.,"Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi, J. et al., "Developments in Diagnosis for Prion Diseases," *Br. Med. Bull.* (1993) 49(4):971–979.

Tateishi et al., "Transmission of Chronic Spongiform Encephalopathy with Kuru Plaques from Humans to Small Rodents," *Ann.Neurol.* (1979) 5:581–584.

Thadani et al., "Creutzfeldt–Jakob Disease Probably Acquired From a Cadaveric Dura Mater Graft," *J. Neurosurg.* (1988) 69:766–769.

Valancius, V. and Smithies, O., "Testing and "In–Out" Targeting Procedure for Making Subtle Genomic Modifications in Mouse Embryonic Stem Cells", *Mol. Cell Biol.* (1991) 11(3):1402–1408.

Westaway et al., Homozygosity for Prion Protein Alleles Encoding Glutamine–171 Renders Sheep Susceptible to Natural Scrapie,: *Genes Dev.* (1994) 8:959–969.

Westaway et al., "Degeneration of Skeletal Muscle, Peripheral Nerves, and the Central Nervous System in Transgenic Mice Overexpressing Wild–Type Prion Proteins," *Cell* (1994) 76:117–129.

Willison et al., "Creutzfeldt–Jakob Disease Following Cadeveric Dura Mater Graft," *Neurosurg. Psychiatric* (1991) 54:940.

Wilesmith, J.W., "The epidemiology of bovine spongiform encephalopathy", *Acad. Press.* (1991) 2:239–245.

DETECTING COW, SHEEP AND HUMAN PRIONS IN A SAMPLE AND TRANSGENIC MICE USED FOR SAME

CROSS-REFERENCE

This application is a continuation-in-part of our earlier filed application Ser. No. 08/692,892 filed Jul. 30, 1996 now U.S. Pat. No. 5,792,901 which is a continuation-in-part of application Ser. No. 08/521,992, filed Aug. 31, 1995, now U.S. Pat. No. 5,908,969 which is a continuation-in-part of our earlier filed application Ser. No. 08/509,261 filed Jul. 31, 1995, now U.S. Pat. No. 5,763,740, which is a continuation-in-part of our earlier filed application Ser. No. 08/242,188, filed May 13, 1994, (issued as U.S. Pat. No. 5,565,186 on Oct. 15, 1996) all of which are incorporated herein by reference in their entirety and to which applications we claim priority under 35 USC §120.

GOVERNMENT RIGHTS

The United States Government may have certain rights in this application pursuant to Grant Nos. NS14069, AG02132, NS22786, AG08967 and AG10770 awarded by the National Institutes of Health.

FIELD OF THE INVENTION

This invention relates generally to methods of assaying and to transgenic animals used in such assays. More specifically, this invention relates to methods of assaying samples for pathogenic bovine prions and to transgenic mice which can be infected with prions which generally only infect cows.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., Science 218: 1309–11 (1982); Prusiner et al., Biochemistry 21: 6942–50 (1982); McKinley et al., Cell 35: 57–62 (1983)]. Complete prion protein-encoding genes have since been cloned, sequenced and expressed in transgenic animals. $PrP^C$ is encoded by a single-copy host gene [Basler et al., Cell 46: 417–28 (1986)] and is normally found at the outer surface of neurons. A leading hypothesis is that prion diseases result from conversion of $PrP^C$ into a modified form called $PrP^{Sc}$. However, the actual biological or physiological function of $PrP^C$ is not known.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," Science 252: 1515–1522 (1991). The most common prion diseases of animals are scrapie of sheep and goats and bovine spongiform encephalopathy (BSE) of cattle [Wilesmith, J. and Wells, Microbiol. Immunol. 172: 21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., Science 197: 943–960 (1977); Medori et al., N. Engl. J. Med. 326: 444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., Neurology 40: 1820–1827 (1990); Goldfarb et al., Science 258: 806–808 (1992); Kitamoto et al., Proc. R. Soc. Lond. (In press) (1994)]. Iatrogenic CJD has been caused by human growth hormone derived from cadaveric pituitaries as well as dura mater grafts [Brown et al., Lancet 340: 24–27 (1992)]. Despite numerous attempts to link CJD to an infectious source such as the consumption of scrapie infected sheep meat, none has been identified to date [Harries-Jones et al., J. Neurol. Neurosurg. Psychiatry 51: 1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., Slow Transmissible Diseases of the Nervous System, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period [Hadlow, W. J., Lancet 2: 289–290 (1959)]. Seven years later, Gajdusek, Gibbs and Alpers demonstrated the transmissibility of kuru to chimpanzees after incubation periods ranging form 18 to 21 months [Gajdusek et al., Nature 209: 794–796 (1966)]. The similarity of the neuropathology of kuru with that of CJD [Klatzo et al., Lab Invest. 8: 799–847 (1959)] prompted similar experiments with chimpanzees and transmissions of disease were reported in 1968 [Gibbs, Jr. et al., Science 161: 388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity [Gibbs, Jr. et al., Slow Transmissible Diseases of the Nervous System, Vol. 2, S. B. Prusiner and W. J. Hadlow, eds. (New York: Academic Press), pp. 87–110 (1979); Tateishi et al., Prion Diseases of Humans and Animals, Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., NINDB Monograph 2, D.C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59: 847–857 (1989)]. SHaPrP differs from MoPrP at 16 positions out of 254 amino acid residues [Basler et al., *Cell* 46: 417–428 (1986); Locht et al., *Proc. Natl. Acad. Sci. USA* 83: 6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. Such a test was first disclosed in parent application Ser. No. 08/242,188 filed May 13, 1994 which is now U.S. Pat. No. 5,565,186 issued Oct. 15, 1996.

More than 45 young adults previously treated with HGH derived from human pituitaries have developed CJD [Koch et al., *N. Engl. J. Med.* 313: 731–733 (1985); Brown et al., *Lancet* 340: 24–27 (1992); Fradkin et al., *JAMA* 265: 880–884 (1991); Buchanan et al., *Br. Med. J.* 302: 824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196: 1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328: 358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307: 517–518 (1993); Cochius et al., *Aust. N. Z. J. Med.* 20: 592–593 (1990); Cochius et al., *J. Neurol. Neurosurg. Psychiatry* 55: 1094–1095 (1992)] as well as at least 11 patients receiving dura mater grafts [Nisbet et al., *J. Am. Med. Assoc.* 261: 1118 (1989); Thadani et al., *J. Neurosurg.* 69: 766–769 (1988); Willison et al., *J. Neurosurg. Psychiatric* 54: 940 (1991); Brown et al., *Lancet* 340: 24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10.) Investigations of the prion diseases have taken on new significance with the reports of more than 20 cases of an atypical, variant CJD (vCJD) in teenagers and young adults [D. Bateman et al., *Lancet* 346: 1155 (1995); T. C. Britton, S. Al-Sarraj, C. Shaw, T. Campbell, J. Collinge, *Lancet* 346: 1155 (1995); G. Chazot et al., *Lancet* 347: 1181 (1996); R. G. Will et al., *Lancet* 347: 921 (1996); S. N. Cousens, E. Vynnyoky, M. Zeidler, R. G. Will, P. G. Smith, *Nature* 385: 197 (1997)]. To date, all of these cases have been reported from Great Britain and France. It now seems possible that bovine prions from "mad cows" passed to humans through the consumption of tainted beef products. It is generally thought that prion contaminated offal initially from sheep and later from cattle was used in the manufacture of meat and bone meal (MBM), and that this is the source of prions responsible for BSE [J. W. Wilesmith, J. B. M. Ryan, M. J. Atkinson, *Vet. Rec.* 128: 199 (1991); N. Nathanson, J. Wilesmith, C. Griot, *Am. J. Epidemiol.* 145: 959 (1997)].

Understanding the species barrier is paramount in our efforts to evaluate the impact of the BSE epidemic in Britain on human health [R. M. Anderson et al., *Nature* 382: 779 (1996)]. It has been estimated that almost one million cattle were infected with BSE prions with an incubation time of about 5 years. This may be an underestimation of the disease incidence as most cattle were slaughtered between 2 and 3 years of age [D. J. Stekel, M. A. Nowak, T.R.E. Southwood, *Nature* 381: 119 (1996)]. Nevertheless, more than 160,000 cattle, primarily dairy cows, have died of BSE over the past decade. In the late 1970s, the hydrocarbon-solvent extraction method used in the rendering of offal began to be abandoned resulting in MBM with a much higher fat content. It is now thought that this change in the rendering process allowed scrapie prions from sheep to survive rendering and to be passed into cattle [J. W. Wilesmith, *Semin. Virol.* 2: 239 (1991); R. H. Kimberlin, *Bovine Spongiform Encephalopathy: The BSE Dilemma* C. J. Gibbs, Jr., Ed. (Springer, New York, 1996) pp. 155–175].

Although many plans have been offered for the culling of older cattle in order to minimize the spread of BSE, it seems more important to monitor the frequency of prion disease in cattle as they are slaughtered for human consumption. No completely reliable, specific test for prion disease in live animals is available [G. Hsich, K. Kenney, C. J. Gibbs, K. H. Lee, M. G. Harrington, *N Engl. J. Med.* 335: 924 (1996)], but immunoblotting of the brainstems of cattle for PrP$^{Sc}$ might provide a reasonable approach to establish the incidence of subclinical BSE in cattle entering the human food chain [J. Hope et al., *Nature* 336: 390 (1988); D. Serban, A. Taraboulos, S. J. DeArmond, S. B. Prusiner, *Neurology* 40: 110 (1990); A. Taraboulos et al., *Proc. Natl. Acad. Sci. USA* 89: 7620 (1992); S.B. Prusiner et al., *J. Infect. Dis.* 167: 602 (1993); K.-U. D. Grathwohl, M. Horiuchi, N. Ishiguro, M. Shinagawa, *J. Virol. Methods* 64: 205 (1997)]. Determining how early in the incubation period PrP$^{Sc}$ can be detected by immunological methods is complicated by the lack of a reliable, sensitive, and relatively rapid bioassay.

SUMMARY OF THE INVENTION

Genetic constructs and methodologies of the invention are used to create animals which due to their genetic make up will develop disease from inoculation with prions which would generally only infect a genetically diverse animal, e.g., a mouse of the invention will consistently become infected with prions which generally will only infect a cow and symptoms of the infection will become apparent in a short period e.g., 350 days or less. The animals of the invention are used in assays to test samples of any given material to determine if the material includes prions which would infect another animal (such as a cow) if the material were ingested or injected.

A preferred transgenic animal of the invention is a mouse with both alleles of its endogenous PrP gene ablated and having therein a bovine PrP gene. When such a mouse is inoculated with prions which generally only infect a cow the transgenic mouse of the invention develops observable symptoms of prion disease in about 350 or more preferably 250 days or less. Transgenic mice containing a bovine PrP gene are designated Tg(BoPrP) and may be crossed with mice with an ablated endogenous PrP gene which are designated Prnp$^{0/0}$ to obtain a hybrid designated Tg(BoPrP)/Prnp$^{0/0}$.

An object of the invention is to provide a transgenic, hybrid, non-human mammal preferably a mouse which has its endogenous PrP gene(preferably both alleles) ablated and which includes a PrP gene from a genetically diverse mammal alone or with a manipulated PrP gene such as a chimeric PrP gene comprised of codons from the host mammal and a genetically diverse mammal.

Yet another object of the invention is to provide for a method of testing samples for the presence of prions. The method involves creating two groups of non-human mammals which have their genome altered so that they are susceptible to infection with prions which generally only infect a genetically diverse animal. The first group of animals is infected with a test sample and the second group is infected with a standardized prion preparation. Both groups of mammals are observed and the presence of prions in the sample can be deduced if the first group of animals develop symptoms of prion infection.

An advantage of the invention is that a standardized prion preparation can be used to provide a control group when testing samples for the presence of prions.

Another object is to provide a transgenic animal (e.g. mouse) with an ablated endogenous PrP gene and an exogenous PrP gene from a genetically diverse animal which transgenic animal is obtained by microinjecting the exogenous PrP gene into an embryonic cell (e.g. a fertilized mouse egg) and implanting the injected cell in a female.

Another object is to provide a hybrid animal which is obtained by crossing an animal (e.g. a mouse) having an ablated endogenous PrP gene with a transgenic animal containing the PrP gene of a genetically diverse animal (e.g. a cow) which gene may be present at elevated levels.

Another object of the invention is to provide a transgenic host mammal (which is small, e.g., less than 1 kg when full grown, and inexpensive to maintain) such as a mouse, rat or hamster which has an ablated endogenous PrP gene and a PrP gene from a genetic diverse large animal (e.g. greater than 2 kg when full grown, and expensive to maintain) such as a human, cow, pig, sheep, cat or dog.

Another object of the invention is to provide a transgenic host animal which includes elevated levels of expression of a native PrP gene of a genetically diverse animal wherein the elevated levels of expression are obtained by the inclusion of a high copy number of the PrP gene of the genetically diverse mammal and/or fusing an enhanced promoter to the PrP gene of the genetically diverse animal which transgenic animal may be used by itself to assay for prions or for cross-breeding with an animal which has an ablated endogenous PrP gene.

An advantage of the present invention is that the transgenic and hybrid animal can be used to assay for the presence of prions (particularly for bovine prions) in a sample in a manner which is substantially faster, more efficient and cheaper than presently available assay methods.

Another advantage is that the transgenic and hybrid animals can detect prions in a sample at very low levels, e.g., 1 part per million, and even as low as 1 part per billion.

Still another advantage is that the transgenic and hybrid animals provide an assay which is highly accurate, i.e., does not provide false positives and consistently determines the presence of prions.

Yet another advantage is that by increasing the copy number of an exogenous PrP gene of the invention in a transgenic or hybrid and disrupting the endogenous PrP gene of, the incubation time for prion caused disease is decreased.

A feature of the present invention is that the transgenic and hybrid animals injected with a sample containing pathogenic prions will consistently develop the disease effects of the prions within a relatively short time, e.g. about 200 days or less after injection.

These and other objects, advantages, and features of the invention will become apparent to those persons skilled in the art upon reading the details of the chimeric gene, assay method, and transgenic mouse as more fully described below.

DETAILED DESCRIPTION OF PREFERRED EMBODIMENTS

Before the present assay methodology and transgenic and hybrid animals used in the assay are described, it is to be understood that this invention is not limited to particular assay methods or transgenic and hybrid animals described, as such methods and animals may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Publications cited here are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Definitions The term "FVB" refers to a mouse strain commonly used in the production of transgenic mice. For purposes of this invention it should be noted that the mouse PrP (PrP) gene is intact and mouse PrP is therefore expressed at normal levels.

The term "Prnp$^{0/0}$ or Prnp-Abl" refers to a transgenic animal which has its PrP gene ablated with the "$^{0/0}$" indicating that both alleles are ablated whereas o/+ indicates only one is ablated. Specifically, the animal being referred to is generally a transgenic mouse which has its PrP gene ablated i.e., a PrP knockout mouse. In that the PrP gene is disrupted no mouse PrP protein is expressed.

The term "sporadic CJD" abbreviated as "sCJD" refers to the most common manifestation of Creutzfeldt-Jakob Disease (CJD). This disease occurs spontaneously in individuals with a mean age of approximately 60 at a rate of 1 per million individuals across the earth.

The term "Iaterogenic CJD" abbreviated as "iCJD" refers to disease resulting from accidental infection of people with human prions. The most noted example of such is the accidental infection of children with human prions from contaminated preparations of human growth hormone.

The term "Familial CJD" refers to a form of CJD which occurs rarely in families and is inevitably caused by mutations of the human PrP gene. The disease results from an autosomal dominant disorder. Family members who inherit the mutations succumb to CJD.

The term "Gerstmann-Strassler-Scheinker Disease" abbreviated as "GSS" refers to a form of inherited human prion disease. The disease occurs from an autosomal dominant disorder. Family members who inherit the mutant gene succumb to GSS.

The term "prion" shall mean an infectious particle known to cause diseases (spongiform encephalopathies) in animals including cows and humans. The term "prion" is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or "mad cow" disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans, cows and other domesticated farm animals.

The terms "PrP gene" and "PrP gene" are used interchangeably herein to describe genetic material which expresses proteins (for example those shown in FIGS. 3–5 of U.S. Pat. No. 5,565,186 issued Oct. 15, 1996) and polymorphisms and mutations such as those listed herein under the subheading "Pathogenic Mutations and Polymorphisms." The PrP gene can be from any animal including the "host" and "test" animals described herein and any and all polymorphisms and mutations thereof, it being recognized that the terms include other such PrP genes that are yet to be discovered.

The terms "standardized prion preparation", "prion preparation", "preparation" and the like are used interchangeably herein to describe a composition containing prions which composition is obtained from brain tissue of mammals which contain substantially the same genetic material as relates to PrP proteins, e.g., brain tissue from a set of mammals which exhibit signs of prion disease which mammals may comprise any of (1) a PrP chimeric transgene; (2) have an ablated endogenous PrP gene; (3) have a high copy number of PrP genes from a genetically diverse species; (4) are hybrids with an ablated endogenous PrP gene and a PrP gene from a genetically diverse species; or (5) combinations of any of 1–4. The mammals from which standardized prion preparations are obtained exhibit clinical signs of CNS dysfunction as a result of inoculation with prions and/or due to developing the disease due to their genetically modified make up, e.g., high copy number of PrP genes.

The term "PrP gene" refers generally to any gene of any species which encodes any form of a PrP amino acid sequences including any prior protein, the non-disease form of the protein being referred to as $PrP^{C}$ and the disease form referred to as $PrP^{Sc}$. Some commonly known PrP sequences are described in Gabriel et al., *Proc. Natl. Acad. Sci. USA* 89: 9097–9101 (1992) and U.S. Pat. No. 5,565,186 both of which are incorporated herein by reference to disclose and describe such sequences.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 of U.S. Pat. No. 5,565,186 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals but may include codons and codon sequences associated with genetic prion diseases such as CJD and codons and sequences not associated with any native PrP gene but which, when inserted into an animal render the animal susceptible to infection with prions which would normally only infect a genetically diverse animal.

The terms "chimeric gene," "chimeric PrP gene", "chimeric PrP gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The term "genetic material related to prions" is intended to cover any genetic material which effects the ability of an animal to become infected with prions. Thus, the term encompasses any "PrP gene", "artificial PrP gene", "chimeric PrP gene" or "ablated PrP gene" which terms are defined herein as well as mutations and modifications of such which effect the ability of an animal to become infected with prions. Standardized prion preparations of the invention are produced using animals which all have substantially the same genetic material related to prion so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene of the present invention or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP gene", "disrupted PrP gene", "ablated PrP gene" and the like are used interchangeably herein to mean an endogenous PrP gene which has been altered (e.g., add and/or remove nucleotides) in a manner so as to render the gene inoperative. Examples of non-functional PrP genes and methods of making such are disclosed in Büeler, H., et al "Normal development of mice lacking the neuronal cell-surface PrP protein" Nature 356, 577–582 (1992) which is incorporated herein by reference. Both alleles of the genes are preferably disrupted.

The terms "hybrid animal", "transgenic hybrid animal" and the like are used interchangeably herein to mean an animal obtained from the cross-breeding of a first animal having an ablated endogenous PrP gene with a second animal which includes either (1) a chimeric gene or artificial PrP gene or (2) a PrP gene from a genetically diverse animal. For example a hybrid mouse is obtained by cross-breeding a mouse with an ablated mouse PrP gene with a mouse containing (1) bovine PrP genes (which may be present in high copy numbers) alone or with (2) chimeric PrP genes. The term hybrid includes any offspring of a hybrid including inbred offspring of two hybrids provided the resulting offspring is susceptible to infection with prions with normal infect only a genetically diverse species and the symptoms of the infection are observable in about 350 days or less, preferably 250 or less.

The terms "susceptible to infection" and "susceptible to infection by prions" and the like are used interchangeably herein to describe a transgenic or hybrid test animal of the invention which develops a prion disease if inoculated with prions which would normally only infect a genetically diverse test animal. The terms are used to describe a transgenic or hybrid animal of the invention such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection). If an animal is susceptible to infection with a particular prion that animal, if inoculated with the prion, will show symptoms of prion disease infection in about 350, preferably 250 days or less.

The term "incubation time" shall mean the time from inoculation of an animal with a prion until the time hen the animal first develops detectable symptoms of disease resulting from the infection. A reduced incubation time is one year or less, preferable about 200 days ±50 days or less, more preferably about 50 days ±20 days or less.

Abbreviations used herein include:
CNS for central nervous system;
BSE for bovine spongiform encephalopathy;
CJD for Creutzfeldt-Jakob Disease;
FFI for fatal familial insomnia;
GSS for Gerstmann-Strassler-Scheinker Disease;
Hu for human;
HuPrP for a human PrP;
Mo for mouse;
Bo for bovine;
MoPrP for a mouse PrP;
SHa for a Syrian hamster;
SHaPrP for a Syrian hamster PrP;
Tg for transgenic;
Tg(SHaPrP) for a transgenic mouse containing the PrP gene of a Syrian hamster;
Tg(HuPrP) for transgenic mice containing the complete human PrP gene;
Tg(ShePrP) for transgenic mice containing the complete sheep PrP gene;
Tg(BoPrP) for transgenic mice containing the complete cow PrP gene;
$PrP^{Sc}$ for the scrapie isoform of the PrP;
$MoPrP^{Sc}$ for the scrapie isoform of the mouse PrP;
MHu2M for a chimeric mouse/human PrP gene wherein a region of the mouse PrP gene is replaced by a corresponding human sequence which differs from mouse PrP at 9 codons;
MBo2M for a chimeric mouse/bovine PrP gene wherein a region of the mouse PrP gene is replaced by a corresponding bovine sequence which differs from mouse PrP at 8 codons.
Tg(MHu2M) mice are transgenic mice of the invention which include the chimeric MHu2M gene;
$MHu2MPrP^{Sc}$ for the scrapie isoform of the chimeric human/mouse PrP gene;
$PrP^{cJD}$ for the CJD isoform of a PrP gene;
$Prnp^{0/0}$ for ablation of both alleles of an endogenous PrP gene, e.g., the MoPrP gene;
$Tg(SHaPrP^{+/0})81/Prnp^{0/0}$ for a particular line (81) of transgenic mice expressing SHaPrP, +/0 indicates heterozygous;
$Tg(BoPrP)/Prnp^{0/0}$ for a transgenic mouse obtained by microinjecting an FVB mouse egg with an ablated PrP gene with a bovine PrP gene (BoPrP);
$Tg(MHu2M)/Prnp^{0/}$ for a mouse with a chimeric (mouse/human) PrP gene (MHu2M) with both alleles of the endogenous mouse PrP gene disrupted;
$Tg(MBo2M)Prnp^{0/0}$ for a mouse with a chimeric (mouse/bovine) PrP gene (MBo2M) with both alleles of the endogenous mouse PrP gene disrupted. FVB for a standard inbred strain of mice often used in the production of transgenic mice since eggs of FVB mice are relatively large and tolerate microinjection of exogenous DNA relatively well.

General Aspects of the Invention

The present invention includes several aspects including:
(1) a transgenic mammal (e.g. a mouse) with elevated levels of expression of a PrP gene of a genetically diverse mammal (e.g. a cow) wherein the elevated levels of expression are obtained by incorporating a high copy number (about 2 to 30 or more) of a native PrP gene of a genetically diverse test animal and/or the inclusion of an enhanced promoter operatively fused to the PrP gene of a genetically diverse animal; (2) a transgenic hybrid animal which is obtained by crossing a animal (e.g. a mouse) having an ablated endogenous PrP gene with an animal with a PrP gene of another genetically diverse animal (e.g. a bovine PrP gene) therein e.g., as per (1) above; (3) a method of determining whether a sample is infected with prions which method involves inoculating a transgenic or hybrid mammal of the invention with a sample to be tested (and preferably simultaneously inoculating identical test animals with a standardized prion preparation for use as controls) and observing the mammal(s) for a period of time sufficient to determine if the mammal(s) develop(s) symptoms of a disease normally associated with prions; (4) a method of testing the efficacy of a drug in the treatment of disease developed as a result of infection with prions comprising administering a drug to be tested to a transgenic or hybrid animal infected with prions (preferably a standardized prion preparation) and observing and/or testing the mammal to determine if the drug aids in treating or slowing the progress of the disease or its symptoms; and (5) a method for determining the cause of death of an animal comprising inoculating a transgenic or hybrid animal of the invention with body fluid or tissue such as extracted brain tissue from the animal which has died (and preferably inoculating control animals with a standardized preparation of prions) and observing the transgenic or hybrid animal (and control animals) in order to determine if the animal(s) develop(s) symptoms of prion infections.

Preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g. rabbits), and Mesocricetus (e.g. hamsters) and Cavia (e.g., guinea pigs). In general mammals with a normal full grown adult body weight of less than 1 kg which are easy to breed and maintain can be used. The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with cow being most preferred. Cows are preferred because an important object of the invention is to use the animal to test a statistically significant number of cows in a herd of cows to determine if the cows are infected with prions which cause BSE, known as "mad cow" disease.

The genetic material which makes up the PrP gene is known for a number of different species of animals [see U.S. Pat. No. 5,565,186 issued Oct. 15, 1996 and Gabriel et al., Proc. Natl. Acad. Sci. USA 89: 9097–9101 (1992)]. Further, there is considerable homology between the PrP genes in different mammals. For example, see the amino acid sequence of mouse PrP compared to human, cow and sheep PrP in FIGS. 3, 4 and 5 of U.S. Pat. No. 5,565,186 wherein only the differences are shown. Although there is considerable genetic homology with respect to PrP genes, the differences are significant in some instances. More specifically, due to small differences in the protein encoded by the PrP gene of different mammals, a prion which will infect one mammal (e.g. a cow) will not normally infect a different mammal (e.g. a mouse). Due to this "species barrier", it is not generally possible to use normal animals, (i.e., animals which have not had their genetic material related to prions manipulated) such as mice to determine whether a particular sample contains prions which would normally infect a different species of animal such as a human. The present invention solves this problem in a surprising manner.

Relationships—PrP Genes:Copy Numbers:Genetic Diversity

Commercially useful transgenic animals are preferably small and easy to reproduce; thus, host animals such as mice, hamsters, guinea pigs and rats are preferred, with mice being most preferred. In order for the transgenic animals to be useful, it is necessary for the animals to be susceptible to infection with prions which normally infect only genetically diverse test animals, and in particular animals of commercial significance for testing, such as humans, cows, horses, sheep, pigs, cats, dogs and chickens, with humans being most preferred. Further, for the transgenic and hybrid animals to be useful in a practical and commercial sense, it is necessary for the animals to demonstrate symptoms of the disease within a relatively short period after inoculation, and for a very high percentage of the animals to demonstrate symptoms of the disease after inoculation e.g., 80% or more of inoculated animals develop clinical symptoms of CNS disease with 350 days or less after inoculation.

In producing a transgenic animal having the above-described characteristics, we noted a number of relationships of significance.

First, it was found that when the entire PrP gene of a hamster was placed in a mouse the transgenic mouse was susceptible to infection with hamster prions.

Second, it was found that when the entire PrP gene of a human was placed in a mouse the mouse was not susceptible to infection with human prions.

Third, it was found that when a chimeric (part human and part mouse) PrP gene was placed in a mouse the mouse was susceptible to infection with human prions.

Fourth, a chimeric gene of cow and mouse PrP genes (corresponding to the human/mouse chimeric) was placed in a mouse and the mouse was not susceptible to infection with cow prions.

A preferred transgenic animal is a mouse with an ablated endogenous PrP gene and a native bovine PrP gene present in a single copy or in a relatively high copy number, in that increasing the copy number tends to decrease the incubation time for the disease once the animal is inoculated with material containing prions.

Notwithstanding such, we now understand that, when the copy number is increased to very high numbers (e.g. 100 copies and above), the transgenic animals may spontaneously demonstrate symptoms of prion disease.

Thus, a most preferred transgenic animal of the invention will include a bovine PrP gene in a sufficiently high copy number so as to shorten the incubation time (e.g. 50 copies ±25) but in a sufficiently low number so as to not initiate spontaneous symptoms characteristic of prion diseases (e.g., not more than 100 copies). It will be understood by those skilled in the art that the number of copies necessary in order to obtain elevated levels of expression of the PrP gene will vary depending upon the particular gene inserted into the particular host. Adjustments can be made to reduce the copy number if the resulting transgenic animals become spontaneously ill. Alternatively adjustments can be made to increase the copy number if the resulting transgenic animals are not subject to infection with prions which normally infect only a genetically diverse animal. Further, adjustments can be made with respect to the use of specific types of enhanced promoters in order to elevate the levels of expression without increasing copy numbers. Specific types of enhanced promoters are known such as neuronal enolase promoters which would provide enhanced expression to the PrP gene without increased copy numbers. The enhanced promoters may operate constitutively or inducibly.

High Copy Numbers

The present invention includes transgenic animals wherein the host animal has its genome changed to include multiple copies (2 or more) of the entire PrP gene of a genetically diverse test animal. Thus, for example, the invention includes transgenic mice and hamsters altered to include two fold or higher levels of expression of the PrP gene of a genetically diverse test animal such as a human, cow or sheep. The two fold or higher levels of expression can be obtained by including higher copy numbers such as 2 to 30 or more copies of the PrP gene of the genetically diverse test animal and/or by including an enhanced promoter which elevates the level of expression of even a low copy number of the gene.

Hybrid Animals

Hybrid animals of the invention can be produced by crossing an animal with an ablated endogenous PrP gene with either of the transgenic animals mentioned above. For example, a mouse containing multiple copies of a bovine PrP gene is crossed with a mouse with a disrupted endogenous PrP gene e.g., Tg($Prnp^{0/0}$). Alternatively, a mouse containing a high copy number of sheep PrP genes (e.g., 50±25) is crossed with a mouse with a disrupted endogenous PrP gene e.g., Tg($Prnp^{0/0}$) to obtain a hybrid mouse Tg(ShPrP)/$Prnp^{0/0}$. A variety of different hybrids can be obtained by crossing an animal with an ablated PrP gene (i.e., a null prion background) with different transgenic animals with different exogenous PrP genes. When successful hybrids are obtained they can be crossed to produce other animals which for the purpose of the disclosure are also considered hybrids if they are susceptible to infection with prions which generally only infect a genetically diverse species. A null prion background means that more than 50% of the endogenous PrP genes are disrupted, preferable more than 80%, more preferable more than 90% and most preferable 100% so that no endogenous PrP is expressed.

Pathogenic Mutations and Polymorphisms

There are a number of known pathogenic mutations in the human PrP gene. Further, there are known polymorphisms in the human, sheep and bovine PrP genes. The following is a list of such mutations and polymorphisms:

TABLE 1

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

The DNA sequence of the human, sheep, cow, cat, dog and chicken PrP genes have been determined allowing, in each case, the prediction of the complete amino acid sequence of their respective proteins. The normal amino acid sequence which occurs in the vast majority of individuals is referred to as the wild-type PrP sequence. This wild-type sequence is subject to certain characteristic polymorphic variations. In the case of human PrP, two polymorphic amino acids occur at residues 129 (Met/Val) and 219 (Glu/Lys). Sheep PrP has two amino acid polymorphisms at residues 171 and 136, while bovine PrP has either five or six repeats of an eight amino acid motif sequence in the amino terminal region of the mature PrP. While none of these polymorphisms are of themselves pathogenic, they appear to influence prion diseases. Distinct from these normal variations of the wild-type PrPs, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc.* Natl. Acad. Sci. USA 89: 9097–9101 (1992). The sequence for the Syrian hamster is published in Basler et al., *Cell* 46: 417–428 (1986). The PrP gene of sheep is published by Goldmann et al., *Proc. Natl. Acad. Sci. USA* 87: 2476–2480 (1990). The PrP gene sequence for bovine is published in Goldmann et al., *J. Gen. Virol.* 72: 201–204 (1991). The sequence for chicken PrP gene is published in Harris et al., *Proc. Natl. Acad. Sci. USA* 88: 7664–7668 (1991). The PrP gene sequence for mink is published in Kretzschmar et al., *J. Gen. Virol.* 73: 2757–2761 (1992). The human PrP gene sequence is published in Kretzschmar et al., *DNA* 5: 315–324 (1986). The PrP gene sequence for mouse is published in Locht et al., *Proc. Natl. Acad. Sci. USA* 83: 6372–6376 (1986). The PrP gene sequence for sheep is published in Westaway et al., *Genes Dev.* 8: 959–969 (1994). These publications are all incorporated herein by reference to disclose and describe the PrP gene and PrP amino acid sequences.

New Approaches To Investigating Bovine Prion Diseases

The importance of animal prion diseases is illustrated by BSE or "mad cow disease" in Great Britain, where >150,000 cattle have died and serious consideration has been given to slaughtering millions of cattle potentially infected with prions. This prion disease BSE is thought to have originated with cattle consuming meat and bone meal produced from sheep offal containing scrapie prions [Wilesmith, J. W., *Semin. Viro.* 2: 239–245].

The BSE epidemic has led to considerable concern about the safety for humans of European beef and other cattle products. Epidemiologic studies over the past two decades have provided much data arguing that humans are unlikely to contract CJD from scrapie-infected sheep products [Harries-Jones et al., *J. Neurol. Neurosurg.*

Psychiatry 51: 1113–1119 (1988); Cousens et al., *J.*

Neurol. Neurosurg. Psychiatry 53: 459–465 (1990); Brown et al., *Neurology* 37: 895–904 (1987)]. There are seven amino acid substitutions which distinguish bovine from sheep PrP which must be considered in drawing conclusions from sheep scrapie about the risk factors to humans from BSE. Whether any of these seven amino acid substitutions render bovine prions permissive in humans remains to be established.

Measuring Levels of Prions

The present invention can be utilized to determine the concentration of prions (which generally only infect a genetically diverse animal) within a given sample. The transgenic mice make it possible to test for the positive presence of prions within a sample. The mice are capable of detecting the presence of prions in a concentration as low as 1 ppm or even 1 ppb or less. The procedure for doing such will be apparent to those skilled in the art upon a review of the present disclosure in combination with an article entitled "Measurement Of The Scrapie Agent Using An Incubation Time Interval Assay," published by Prusiner, et al, *Annals. of Neurology* 11: 353–358 (1982) which is incorporated herein by reference to disclose such a method of measurement. In general, the method is carried out by determining the titer of the prions by carrying out measurements of time intervals from inoculation to onset of symptoms and from inoculation to death. The intervals are inversely proportioned to the size of the dose injected intracerebrally. The logarithms of the time intervals minus a time factor are linear functions of the logarithms of the inoculum size.

An Epitope Modulating Prion Transmission

Hu prions were used to infect to Tg(MHu2M) mice in U.S. Pat. No. 5,565,186. Thus, the resistance of Tg(MBo2M) mice to BSE prions was puzzling (Table 3). A comparison of the MoPrP-A, MBo2M PrP, and MHu2M PrP translated sequences shows that Hu residue substitutions in MHu2M extended from 97 to 168 while Bo substitutions in MBo2M extended from 97 to 186. This finding raised the possibility that residues 184 and 186, which are not homologous in Bo and Mo PrP and lie at the COOH-terminal end of the chimeric region, might account for the differences in susceptibility of Tg(MHu2M) and Tg(MBo2M) mice to prion infection (Table 4). Alternatively, residue 203, which is a Val in Mo and Hu PrP and is an Ile in BoPrP, might be responsible for this difference in susceptibility to prions. In Tg(MBo2M) mice, residue 203 is a Val and thus, it might prevent conversion of MBo2M $PrP^C$ into $PrP^{Sc}$.

The availability of three-dimensional structures for the Mo PrP(121–231) and SHa PrP(90–231) PrP fragments [R. Riek et al., *Nature* 382: 180 (1996); T. L. James et al., *Proc. Natl. Acad. Sci. USA* 94: 10086 (1997)] and more recently the full-length SHa(29–231) [D. G. Donne et al., *Proc. Natl. Acad. Sci. USA (in press)*] has allowed us to view the impact of changes in the PrP sequence in a spatial context. This led us to understand the sequentially disparate but spatially proximal epitope that provides the $PrP^C$/protein X binding interface [K. Kaneko et al., *Proc. Natl. Acad. Sci. USA* 94: 10069 (1997)]. With this in mind, we studied the spatial juxtaposition of the residues that contribute to the Hu/Bo species barrier that we believe form a subset of the $PrP^C/PrP^{Sc}$ binding interface. Residues 184, 186, 203 and 205 were identified within the three-dimensional structure of SHa PrP(90–231) derived by solution NMR. These residues are seen to cluster on one side of the $PrP^C$ structure and are spatially distinct from the discontinuous epitope consisting of residues 168, 172, 215 and 219 that binds to the protein that makes the conversion of $PrP^C$ to $PrP^{Sc}$ possible. To this collection of residues, we added those known to be polymorphic from an extensive analysis of the PrP genes from over forty species [P. Bamborough et al., *Cold Spring Harb. Symp. Ouant. Biol.* 61: 495 (1996)]. These residues are candidates for contributing to the species barrier. Almost all of these residues cluster and enlarge the epitope formed by residues 184, 186, 203 and 205. Certainly, other residues (e.g. 204) that are spatial neighbors of these residues are candidates for this epitope. Their mutation would be expected to create a species barrier. A systematic study of residues that should contribute to this epitope will allow us to define the extent of the $PrP^C/PrP^{Sc}$ interface and thus reach an understanding of the species barrier at a molecular level. This epitope includes regions that are known to remain structurally constant as well as a portion that is known to undergo a substantial conformational reorganization. Perhaps this explains why $PrP^{Sc}$ can homodimerize as well as bind to $PrP^c$ and simultaneously act as a template for assisting the conversion of $PrP^C$ into $PrP^{Sc}$. Transgenic studies have shown that some mutations associated with inherited human disease create transmissible disease (178, 200, 210) while others create disease in the founder's lineage that are not transmissible to murine hosts expressing wild-type PrP (e.g. 102). Seven point mutations (178, 180, 183, 198, 200, 208, 210) known to cause inherited prion diseases including those that are known to create a transmissible encephalopathy map to this region of the structure as well.

Designing Transgenes

The identification of a species specific epitope that modulates the conversion of $PrP^C$ into $PrP^{Sc}$ has important implications for the design of PrP transgenes. Bo/Mo chimeric transgenes could contain Mo or Bo residues at positions 184, 186, 203 and 205 in different combinations designed to obtain the desired results. It should also be possible to construct improved Hu/Mo chimeric transgenes by simultaneously mutating Hu residues at these same positions to Mo residues. Mutagenesis at any or all of these positions may overcome the paradoxically long incubation times found in Tg(MHu2M)Prnp$^{0/0}$ mice expressing high levels of the transgene product as well as the resistance of Tg(MBo2M) mice to Bo prions (Table 3).

Implications for Public Health and Monitoring the Food Supply

The Tg(BoPrP) mice make possible, for the first time, an accurate determination of BSE prion titers in brain and other tissues. Determining the titers of BSE prions in muscle, pancreas, liver and intestine that are commonly consumed by humans will be of utmost importance. If the current cases of vCJD are due to bovine prions, then it is likely the exposure occurred prior to the specified bovine offals ban of November 1989 that prohibited human consumption of CNS and lymphoid tissues from cattle older than 6 months of age. This legislation was based upon studies in sheep showing that the highest titers of scrapie prions are found in these tissues. In those scrapie studies, sheep tissues were inoculated into non-Tg Swiss mice which are slightly more susceptible to sheep prions than bovine prions. Because the bioassay for bovine prions in ordinary mice is so insensitive, the levels of prions in bovine muscle remain unknown. If the distribution of bovine prions proves to be different from that presumed from sheep then assumptions about the efficacy of the offal ban will need to be reassessed.

These Tg(BoPrP) mice also make possible for the first time the evaluation of drugs and other medicinal products derived cattle for prion contamination. For example, collagen from cattle is used widely in plastic and reconstructive surgery and gelatine is used in foods and in the production of a wide variety of drug capsules. The availability of Tg(BoPrP) mice will also make possible epidemiologic studies on the frequency of BSE in countries such as the United States and Canada which have been thought to be spared. With these Tg(BoPrP) mice, it is now possible to determine whether or not it will be important to produce Tg cattle that are resistant to prions by genetic ablation of the PrP gene or constructing transgenes which interrupt the formation of $PrP^{Sc}$ from $PrP^{C}$.

EXAMPLES

The following examples are put forth so as to provide those of ordinary skill in the art with a complete disclosure and description of how to make and use the standardized preparation, chimeric genes, transgenic mice and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Transgenic Mice Expressing BoPrP and MBo2M PrP

Procedures were carried out to construct Tg(BoPrP) mice using FVB mice which express MoPrP-A. Two lines, designated Tg(BoPrP)883 and Tg(BoPrP)333, were obtained. The transgene used to construct these lines was eventually found to be defective since neither line expressed BoPrP at levels detectable by Western blotting when tested using antisera specific for BoPrP [see U. Oberdieck, *Arch. Virol.* 36: 99 (1994)]. Because both Tg lines expressed MoPrP-A ($Prnp^{a}$) genes, the mice as $Prnp^{a/a}$ were used as controls. These mice made it possible to assess the remote possibility that sequences other than PrP within the cosTet vector could influence the specificity for passaging of BSE prions.

Example 2

Success in transmitting Hu prions to Tg(MHu2M) mice per U.S. Pat. No. 5,565,186 prompted us to construct similar mice expressing MBo2M PrP. Mice deficient for PrP ($Prnp^{0/o}$) were crossed onto the FVB background and used as recipients for microinjection [see H. Bueler et al., *Nature* 356: 577 (1992)]. Three Tg(MBo2M)$Prnp^{0/0}$ founders were obtained. Only two were fertile and could be bred for preliminary screening for expression of MBo2M PrP. Of these, one expressed only low levels of MBo2M PrP. The other line, Tg(MBo2M) 14586/$Prnp^{0/0}$, was found to express approximately 8–16×the amount of MBo2M PrP per g of total protein when compared to bovine brain. The latter line was selected for transmission studies.

Example 3

In a parallel study, a new BoPrP transgene was constructed in order to create lines of Tg(BoPrP) mice which efficiently express BoPrP. To ensure that any interfering effects of endogenous PrPs were eliminated FVB/$Prnp^{0/0}$ mice were used as recipients for microinjection. Four lines of Tg(BoPrP)/$Prnp^{0/0}$ mice were established; two of these, Tg(BoPrP)4092/$Prnp^{0/0}$ and Tg(BoPrP)4125/$Prnp^{0/0}$, express 4–8×and 8–16×more BoPrP per g of protein than that found in bovine brain, respectively.

Example 4

Resistance of Tg(MBo2M) Mice to Infection with BSE Prions

Extracts prepared from the brainstems of several cows with histologically positive BSE and $PrP^{Sc}$ by Western blotting were inoculated into Tg(MBo2MPrP) mice. None of the mice developed clinical signs of neurologic dysfunction, more than 600 d after inoculation (Table 3).

This was surprising since the MBo2M ORF was comprised of BoPrP and MoPrP-A sequences, and previous studies had shown that $Prnp^{a}$ mice are susceptible to BSE, with incubation times exceeding 400 d. That the inocula used for intracerebral injection of the Tg(MBo2M)PrP mice contained infectious prions was shown by transmission of prion disease to FVB, Tg(BoPrP)883 and Tg(BoPrP)333 mice expressing MoPrP-A. These mice exhibited incubation times of 400–650 d (Table 3), similar to that reported by others [H. Fraser, M. E. Bruce, A. Chree, I. McConnell, G. A. H. Wells, *J. Gen. Virol,* 73: 1891 (1992)]. Two of 18 Tg(MoPrP-A)4053 mice inoculated with BSE prions have exhibited signs of CNS dysfunction at ~350 d (Table 3). In contrast, these mice inoculated with RML Mo prions develop disease in −50 d [G. A. Carlson et al., *Proc. Natl. Acad. Sci. USA* 91: 5690 (1994)]. Thus, Tg(MBo2MPrP) mice were highly resistant to BSE prions while mice expressing wild-type Mo PrP-A sequence were susceptible to BSE prions but required prolonged incubation times.

Example 5

Susceptibility of Tg(BoPrP) Mice to BSE Prions

Two lines of Tg(BoPrP)$Prnp^{0/0}$ mice expressing BoPrP were inoculated with a 10% homogenate derived from the medulla of a Hereford bull (case PG31/90) clinically ill with BSE. The Tg(BoPrP)4125/$Prnp^{0/0}$ mice with the highest level of BoPrP expression were found to be highly susceptible to BSE prions, with 100% of animals exhibiting clinical signs within 250 d following inoculation. Tg(PoPrP)4092/$Prnp^{0/0}$ mice with an intermediate level of BoPrP expression exhibited a longer incubation period with the same inoculum; they had a mean incubation period of ~320 d. Similar incubation times were obtained when these Tg lines were inoculated with another BSE isolate (Table 3).

Example 6

Neuropathology of BSE in Tg(BoPrP) Mice

The neuropathology of both lines of Tg(BoPrP) mice infected with either of two BSE isolates were examined:

PG31/90 and GJ248/85. The distribution of spongiform degeneration was similar to that previously reported in cattle afflicted with BSE [G. A. H. Wells and J. W. Wilesmith, *Brain Pathol.* 5: 91 (1995)]. Spongiform degeneration was most intense in the thalamus, hypothalamus, and tegmentum of the midbrain, pons, and medulla. Like ESE in cattle, there was little or no vacuolation in the cerebral cortex of basal ganglia. It should be noted that this contrasts with virtually all Mo passaged scrapie-strains where we observe vacuolation of the cerebral cortex [H. Fraser and A. G. Dickinson, *J. Comp. Pathol.* 83: 29 (1973); S. J. DeArmond and S. B. Prusiner, *Am. J. Path.* 146: 785 (1995)]. The pattern of neuropathology in Tg(BoPrP) mice differed from that of BSE in cattle by the absence of vacuolation in the nucleus of the spinal trigeminal tract, the nucleus of tractus solitarius, and the periaqueductal grey of the midbrain. The midbrain is where the most intense vacuolation in cattle was found. $PrP^{Sc}$ colocalized with vacuolation in the Tg(BoPrP) mice when visualized using either PrP immunohistochemistry of hydrolytic autoclaving. No amyloid plaques were identified by H&E stain or by PrP immunohistochemistry.

Example 7

Localization of $PrP^{Sc}$ in the Brains of TG(BoPrP) Mice

Histoblotting demonstrated $PrP^{Sc}$ deposition highly localized to the brainstem of Tg(BoPrP)4125/Prnp$^{0/0}$ mice. For these studies, an anti-PrP rabbit polyclonal antiserum designated #9095 was raised against a synthetic peptide corresponding to residues 90–145 of BoPrP. This antiserum shows a broad specificity, with a high affinity for bovine, mouse, human, hamster, and sheep PrPs. We compared the pattern of $PrP^{Sc}$ accumulation in Tg(BoPrP) mice inoculated with BSE prions with the pattern in congenic B6.I-1 (Prnp$^{b/b}$) mice inoculated with 301V prions. The 301V strain was derived following transmission of BSE prions to Prnp$^{b/b}$ mice [M. Bruce et al., *Phil. Trans. R. Soc. Lond.* B343: 405 (1994)]. While the patterns of $PrP^{Sc}$ accumulation were virtually identical in the brainstem there were marked differences in the accumulation patterns in the diencephalon and cerebral cortex. In Tg(BoPrP) mice, there was diffusely scattered, patchy accumulation of $PrP^{Sc}$ in the thalamus, whereas the entire thalamus was strongly immunoreactive for $PrP^{Sc}$ in B6.I-1 mice. In Tg(BoPrP) mice, there were a few punctate deposits of PrP in the cerebral cortex, whereas there was significantly more $PrP^{Sc}$ in the cerebral cortex of B6.I-1 mice which deposited in a laminar fashion. The accumulation of $prP^{Sc}$ in the brainstems of Tg(BoPrP) mice inoculated with BSE prions is reminiscent of the pattern of $PrP^{Sc}$ accumulation in cow brains infected with BSE. The distribution of $PrP^{Sc}$ in Tg(BoPrP) brain was more extensive than the distribution of vacuolar degeneration.

The ability of the Tg(BoPrP)Prnp$^{0/0}$ mice to mimic the CNS distribution of $PrP^{Sc}$ found in cattle with BSE is reminiscent of the ability of Tg(MHu2M) mice to mimic the distribution of $PrP^{Sc}$ deposition in two of the inherited prion diseases. Fatal familial insomnia (FFI) is caused by the N178D mutation while one form of familial (f) CJD is caused by the E200K mutation [Medori et al., *N. Engl. J. Med.* 326: 444 (1992)]. Transmission of FFI prions from human brain to Tg(MHu2M) mice produced marked accumulation of $PrP^{Sc}$ confined to the thalamus similar to that found in humans with FFI; in contrast, fCJD(E200K) prions resulted in $PrP^{Sc}$ deposition throughout the cortex, thalamus, and hypothalamus as seen in humans with fCJD(E200K) [Telling et al., *Science* 274: 2079 (1996)].

Example 8

Characteristics of $PrP^{Sc}$ in the Brains of Tg(BoPrP) Mice $PrP^{Sc}$ was identified in brains of Tg(BoPrP) mice afflicted with BSE by Western blotting using anti-PrP rabbit polyclonal 9095 antiserum. Both the Tg(BoPrP)4125/Prnp$^{0/0}$ and Tg(BoPrP)4092/Prnp$^{0/0}$ lines were found to contain large amounts of a protein of ~34 kD, indistinguishable in size from that found in the bovine PG31/90 brain from which the BoPrP ORF used to construct the transgene was derived. The increased size of the BoPrP compared to MoPrP is predominantly due to the presence of six octarepeats rather than five. In addition to the extra octarepeat, the NH$_2$-terminal region contains two single base insertions relative to SHa/Hu PrP; however the region corresponding to residues 90–231 is identical in size to SHa/Hu PrP.

Following digestion with proteinase K, a series of truncated polypeptides of ~28 kD, ~23 kD and ~17 kD were revealed in BSE-infected PG31/90 brain corresponding to the diglycosylated, monoglycosylated and unglycosylated form, respectively. Indistinguishable patterns of protein-resistant BoPrP fragments were identified in Tg(BoPrP) 4092/Prnp$^{0/0}$ brains infected width either PG31/90 or GJ248/85 brain inocula, and, in slightly lower amounts, in Tg(BoPrP)4125/Prnp$^{0/0}$. Interestingly, the ratios of the three glycoforms were similar in bovine and Tg(BoPrP) mouse brains and in those reported for vCJD patients [J. Collinge, K. C. L. Sidle, J. Meads, J. Ironside, A. F. Hill, *Nature* 383: 685 (1996)] with a predominance of the fully glycosylated fragment. BSE prions passaged into normal Prnp$^{a/a}$ mice showed a similar pattern of protease resistant fragments but these displayed a slightly lower molecular size compared to BoPrP$^{Sc}$ found in the brains of BSE-infected Tg(BoPrP) mice and cattle or to the MoPrP$^{Sc}$ fragments observed following hydrolysis of brain extracts of Prnp$^{a/a}$ mice which had been inoculated with a sheep scrapie isolate.

While the origin of the bovine prions causing BSE cannot be determined by examining the amino acid sequence of $PrP^{Sc}$ in cattle with BSE, the availability of Tg(BoPrP) Prnp$^{0/0}$ mice provide new insights into the origin of this epidemic. It will be of considerable interest to examine bovine specimens collected at various times and locations throughout the epidemic to study strains of BSE prions. Studies with eight BSE inocula injected into several strains of inbred mice contend that a single strain of BSE prions is found in all infected cattle. However, these results may be flawed since new strains often emerge after passage across species. Determining the extent of BSE prion diversity using Tg(BoPrP)Prnp$^{0/0}$ mice should prove most informative.

Example 9

Measuring Bovine Prions

Mice inoculated intracerebrally with BSE brain extracts require more than a year to develop disease.

Depending on the titer of the inoculum, the structures of PrP$^C$ and PrP$^{Sc}$, and other host factors, the number of inoculated animals developing disease can vary over a wide range. Some investigators have stated that transmission of ESE to mice is quite variable with incubation periods exceeding one year [Lesmazas et al., *Science* 275: 402 (1997)]. However, others report a low prion titer of $10^{2.7}$ ID$_{50}$ units/ml of 10% BSE brain homogenate compared to $10^7$–$10^9$ ID$_{50}$ units/ml in rodent brain [Hunter et al., *Res. Vet. Sci.* 4: 543 (1963)]. Moreover, endpoint titrations of BSE prions in cattle suggest that the titer of prions in bovine brains exceeds $10^6$ $ID_{50}$ units/ml.

Other attempts at assaying BSE prions have used animals from various species. Brain extracts from BSE cattle cause disease in cattle, sheep, mice, pigs, and mink after intracerebral inoculation. However, prions in brain extracts from sheep with scrapie fed to cattle produced illness substantially different from BSE [M. M. Robinson et al., *J. Comp. Path.* 113: 241 (1995)]. All of the previously available bioassay systems suffer from severe limitations which limit their usefulness. Apart from the cost involved, the long incubation periods and low efficiency of transmission of prions, heightened in some cases by the species barrier caused by lack of PrP sequence identity, have conspired to severely impede progress in performing routine measurements of titers of BSE prions.

Example 10

Comparative Example

Tg(HuPrP) Mice Are Resistant to Human Prions

Tg mice expressing HuPrP were produced using the HuPrP gene ORF, which had been cloned into the cosSHa.Tet expression vector [Scott et al., *Protein Sci.* 1: 986–997 (1992)]. Microinjection of outbred C57B6/SJL and inbred FVB mouse embryos resulted in two founder transgenic animals designated Tg(HuPrP)B6SJL-110 and Tg(HuPrP)FVB-152. We estimated by serial dilution of brain homogenates and immuno dot blotting, that the level of $prP^c$ in the brains of the progeny of these founders express HuPrP at levels 4- to 8-fold higher than the level of HuPrP found in the human brain.

To determine whether expression of HuPrP in Tg(HuPrP) B6SJL-110 and Tg(HuPrP)FVB-152 conferred susceptibility to human prions, incubation periods were measured after inoculation of Tg(HuPrP) and non-Tg mice with brain extracts from 18 patients that had died of sporadic CJD, iatrogenic CJD, familial CJD or GSS. From experiments performed over the past 2.5 years, we concluded that the two lines of Tg(HuPrP) mice were no more responsive than non-Tg mice to human prions (see Table 2 below). The rate of transmission to Tg(HuPrP) mice was 8.3% (14 clinically sick mice out of 169 mice) which was similar to a transmission rate of 10.3% in control non-Tg mice (6 clinically sick mice out of 58 mice). In the infrequent event of a positive transmission, incubation times were extremely long ranging, from 590 days to 840 days in both Tg(HuPrP) and non-Tg mice. By this late time, many animals had died of intercurrent illnesses which complicated diagnosis. The difficulty of interpreting transmissions occurring after extremely long incubation periods is compounded by the heightened potential for artifactual results due to low levels of contaminating prions.

Statistical analysis shows that the frequency of Hu prion transmission to Tg(MHu2MPrP) mice compared to Tg(HuPrP) and non-Tg mice is highly significant using the Fisher's exact test, $p<10^{-7}$ [Mehta et al., *J. Am. Stat. Assn.* 78:(392) 427–434 (1983)]. When Hu prion transmission to Tg(HuPrP) mice was compared to non-Tg mice, the frequencies were similar, $p=0.79$.

To confirm the clinical diagnosis of prion disease, 5 ill Tg(HuPrP) and 1 non-Tg mice were sacrificed and brain extracts were examined for the presence of $PrP^{Sc}$ by Western blotting with the α-PrP antibodies, 3F4 mAb and R073 antiserum [Kascsak et al., *J. Virol.* 61: 3688–3693 (1987); Serban et al., *Neurology* 40: 110–117 (1990)]. The 3F4 mAb reacts specifically with HuPrP allowing discrimination from MoPrP. $MoPrP^{Sc}$ was detected in the brain of the non-Tg mouse inoculated with sporadic CJD inoculum #87011 which developed clinical signs after 756 days, while 3F4-reactive $PrP^{Sc}$ was detected in the brains of two Tg(HuPrP) mice which developed clinical signs after 589 days post-inoculation with iatrogenic CJD inoculum #170. The equivalent transmission rates of human prions in Tg(HuPrP) and non-Tg mice indicate that this is a rare event with the same frequency of occurrence as the stochastic conversion of $MoPrP^C$ to $MoPrP^{Sc}$ induced by human prions.

The absence of either R073- or 3F4-reactive $PrP^{Sc}$ in the brains of 3 out of the 6 mice analyzed may reflect the difficulty of accurately diagnosing prion disease in elderly animals. Some of the mice inherited prion diseases of both humans and Tg mice exhibit little or undetectable levels of protease-resistant PrP; yet, based on transmission studies, their brains contain prions and they show clear spongiform degeneration [Medori et al., *N. Engl. J. Med.* 326: 444–449 (1992)].

In contrast to Tg(MHu2M) mice, Hu prions from patient RG have not transmitted to either Tg(HuPrP) or non-Tg mice after >330 days (see Table 2 below). Attempts to transmit preparations enriched for Hu prion rods prepared from the brain of patient RG have likewise been negative for >300 days. In addition, inoculum from the iatrogenic CJD case (#364) has produced illness in neither Tg(HuPrP) nor non-Tg mice after >780 days (as shown in Table 2 below).

TABLE 2

Incubation times in Tg(HUPrP)FVB-152 and Tg(HUPrP)B6SJL-110 mice after inoculation with brain extracts from patients with human prion diseases

| Host | Inoculum | $(n/n_o)^a$ | Incubation times (days ± SE)[b] |
|---|---|---|---|
| Tg152 | Sporadic CJD (#87011) | 1/10 | 706 |
| Non-Tg | Sporadic CJD (#87011) | 3/5 | 697.3 ± 51 |
| Tg 152 | Sporadic CJD (#88037) | 3/10 | 680 ± 28 |
| Tg 152 | Sporadic CJD (RG) | 0/10 | |
| Non-Tg | Sporadic CJD (RG) | 0/10 | |
| Tg 152 | Sporadic (RG) Rods | 0/8 | |
| Non-Tg | Sporadic (RG) Rods | 0/8 | |
| Tg 152 | Codon 102 GSS (#87027) | 4/10 | 724 ± 16 |
| Non-Tg | Codon 102 GSS (#87027) | 0/10 | 679 |
| Tg 152 | Codon 102 GSS (#87031) | 0/10 | |
| Non-Tg | Codon 102 GSS (#87031) | 1/5 | 742 |
| Tg 152 | Codon 178 F-CJD | 0/8 | |
| Non-Tg | Codon 178 F-CJD | 0/8 | |
| Tg 110 | Sporadic CJD (#87036) | 0/8 | |
| Non-Tg | Sporadic CJD (#87036) | 1/5 | 838 |
| Tg 110 | Iatrogenic CJD (#703) | 0/10 | |
| Non-Tg | Iatrogenic CJD (#703) | 0/5 | |

TABLE 2-continued

Incubation times in Tg(HUPrP)FVB-152 and
Tg(HUPrP)B6SJL-110 mice after inoculation with brain
extracts from patients with human prion diseases

| Host | Inoculum | $(n/n_o)^a$ | Incubation times (days ± SE)$^b$ |
|---|---|---|---|
| Tg 110 | Iatrogenic CJD (#170) | 2/10 | 589 ± 0 |
| Non-Tg | Iatrogenic CJD (#170) | 0/5 | |
| Tg 110 | Iatrogenic CJD (#364) | 0/10 | |
| Non-Tg | Iatrogenic CJD (#364) | 0/5 | |
| Tg 110 | Codon 200 F-CJD | 1/8 | 791 |
| Tg 110 | Codon 217 GSS | 1/8 | 874 |
| Tg 110 | Codon 102 GSS-A | 0/10 | |
| Tg 110 | Codon 102 GSS-B | 1/8 | 694 |
| Tg 110 | Codon 117 GSS | 0/8 | |

$^a$Number of animals developing clinical sickness divided by the total number of animals inoculated.
$^b$Refers to time to diagnosis of illness.

Patients from which inoculum were derived are described in the following publications: [Collinge et al., *Lancet* 337: 1441–1442 (1991); Hsiao et al., *Nature* 338: 342–345 (1989); Hsiao et al., *Neurology* 41: 681–684 (1991)].

TABLE 3

Susceptibility and resistance of transgenic mice to BSE prions

| Inoculum | Recipient | Trans-gene Expression | Incubation Time (days ± S.E.) | n/no$_o$ |
|---|---|---|---|---|
| A. Mice deficient for Prp (Prnp$^{0/0}$) | | | | |
| BSE(PG31/90) | Tg(BoPrP)4125 | 8–16X | 234 ± 8 | 10/10 |
| BSE(PG31/90) | Tg(BoPrP)4092 | 4–8X | 319 ± 15 | 8/8 |
| BSE(GJ248/85) | Tg(BoPrP)4125 | 8–16X | 210 ± 28 | 6/10 |
| BSE(GJ248/85) | Tg(BoPrP)4092 | 4–8X | 330 ± 13 | 5/8 |
| BSE(GJ248/85) | Tg(MBo2M)14586 | 8–16X | >600 | 0/15 |
| BSE(PG31/90) | Tg(MBo2M)14586 | 8–16X | >600 | 0/13 |
| BSE(574C) | Tg(MBo2M)14586 | 8–16X | >600 | 0/13 |
| B. Mice expressing MoPrP-A | | | | |
| BSE(GJ248/85) | FVB | 0 | 628 ± 47 | 2/3 |
| BSE(PG31/90) | FVB | 0 | 448 ± 29 | 2/2 |
| BSE(574C) | FVB | 0 | 525 ± 34 | 4/4 |
| BSE(PG31/90) | Tg(MoPrP-A)4053 | 8–16X | >350 | 2/18 |
| BSE(PG31/90) | Tg(BoPrP-A)333 | 0* | 426 ± 11 | 8/8 |
| BSE(PG31/90) | Tg(BoPrP-A)833 | 0* | 395 ± 22 | 9/9 |
| BSE→Tg(BoPrP)333 | CD-1 | 0 | 163 ± 5 | 8/8 |
| BSE→Tg(BoPrP)333 | CD-1 | 0 | 148 ± 0 | 8/8 |

*No BoPrP was detected by Western Immuunoblotting.

TABLE 4

Variations in amino acid residue that seem to modulate
the transmission of prions from one species to another.

| PrP gene | 138* | 184 | 186 | 203 | 206 |
|---|---|---|---|---|---|
| Mouse | M | I | Q | V | M |
| Bovine | L | V | E | I | M |
| MBo2M | L | V | E | V | M |
| Human | I | I | Q | V | M |
| MHu2M | I | I | Q | V | M |
| Sheep | L | V | Q | I | I |

*Residue numbers correspond to HuPrP.

Example 11

The Susceptibility of Tg(BoPrP)Prnp$^{0/0}$ Mice to BSE Prions

BoPrP or MBo2M PrP were ligated into the cosTet vector for microinjection. MBo2M PrP was constructed as described previously for similar chimeric PrP transgenes (see U.S. Pat. No. 5,565,186) resulting in eight bovine substitutions in MoPrP corresponding to HuPrP residues: 97, 109, 138, 143, 145, 155, 184 and 186. Fertilized oocytes from FVB/Prnp$^{0/0}$ mice were produced by repeated backcrosses of Prnp$^{0/0}$ mice (20) with FVB mice obtained from Charles River Laboratories. Founder Tg(BoPrP)Prnp$^{0/0}$ and Tg(MBo2M)Prnp$^{0/0}$ mice were identified by PCR screening for transgene integration using a Beckman robotic workstation. Tg mice from the F2 generation were sacrificed and the level of BoPrPC expression in the brain was determined by dot blot using two-fold dilutions of the homogenate that were compared to BoPrPC in bovine brain. Tg(BoPrP) Prnp$^{0/0}$ mice from lines chosen for transmission studies were inoculated intracerebrally with 30 μl of a 10% homogenate of the medulla prepared with phosphate-buffered saline. The medulla was from a Hereford bull afflicted with BSE (PG31/90) with histologically and biochemically verified BSE. The well-being of the mice was monitored daily while the neurologic status was assessed semi-weekly. Mice were scored positive for prion disease when two of three signs of neurologic dysfunction were present and progressive deterioration of the animals was apparent. Most reliable signs of neurologic dysfunction for monitoring prion disease in mice are (i) truncal ataxia, (ii) increased tone of the tail, and (iii) lack of forelimb extensor response when lifted by the tail [see Scott et al., *Cell* 59: 847 (1989)].

Neuropathology of Tg(BoPrP)Prnp$^{0/0}$ Mice Inoculated with BSE Prions

No pathological changes were found in the periaqueductal grey of the midbrain. Mild to moderate vacuolar degeneration was found in the reticular formation of the midbrain tegmentum. Reactive astrocytic gliosis colocalized with sites of vacuolar degeneration: astrogliosis in the red nucleus was observed. Little or more vacuolar degeneration was found in the tract or the nucleus of the spinal tract of the trigeminal nerve in the medulla. Moderate to severe vacuolar degeneration occurred in the medial tegmentum of the medullary reticular formation. Small PrP-immunopositive primitive plaque-like deposits were co-localized with sites of the severest vacuolar degeneration. Hematoxylin and eosin stain was used.

Regional Distribution of PrP$^{Sc}$ in the Brains of Tg (BoPrP) Mice Inoculated with BSE Prions Tg(BoPrP)Prnp$^{0/0}$ mouse inoculated with BSE prions from bovine brainstem was sacrificed after exhibiting signs of CNS dysfunction. Cryostat sections were taken through the hippocampus and thalamus, and the brainstem were transferred to nitrocellulose, digested with proteinase K and immunostained. Congenic B6.I-1 (Prnp$^{b/b}$) mice were inoculated with 301V prions and processed as described above.

Sections taken through hippocampus and thalamus, and the brainstem were immunostained. The anti-PrP rabbit polyclonal antiserum designated #9095 was raised against a synthetic peptide corresponding to residues 90–145 of BoPrP. Three rabbits were immunized with 0.25 mg of the peptide dispersed into complete Freund's adjuvant and booster immunizations performed with 0.25 mg of the peptide in RIBI adjuvant. The antiserum was used at a dilution of 1: 1000 for histoblotting. The antiserum reacted strongly with PrP from cattle, mice, Syrian hamsters and humans.

The instant invention is shown and described herein in what is considered to be a most practical and preferred embodiments. It is recognized, however, that departures may be made from which are within the scope of the invention and that modifications will occur to one who is skilled in the art upon reading this disclosure.

We claim:

1. A transgenic mouse comprising:
   (a) a genome wherein both alleles of an endogenous PrP gene are ablated; and
   (b) a transgene expressing an exogenous PrP gene from a genetically diverse mammal selected from the group consisting of cow, sheep and human;
   wherein the mouse is susceptible to infection with prions which generally will only infect the genetically diverse test mammal of the species from which exogenous PrP gene was obtained, and further wherein the mouse exhibits symptoms of prion disease within 200 days or less after inoculation.

2. The mouse of claim 1, wherein the expression of the exogenous PrP gene is at a level which is two fold or more greater than the normal level of expression of the endogenous mouse PrP gene.

3. The mouse of claim 1, wherein the exogenous PrP gene is a bovine PrP gene.

4. A method of testing a sample for the presence of prions, comprising:
   inoculating a mouse comprising (a) a genome wherein both alleles of an endogenous PrP gene are ablated and (b) an expressed exogenous PrP gene from a genetically diverse mammal selected from the group consisting of cow, sheep and human with prions which generally will only infect a genetically diverse test mammal; and
   observing the mouse for symptoms of prion infection within 200 days of inoculation.

5. The method of claim 4, wherein the sample used to inoculate the mouse is selected from the group of samples consisting of (a) a pharmaceutical formulation containing a therapeutically active component extracted from a mammalian source, (b) an organ, extract a tissue extract, body fluid or cells extracted from a mammalian source, (c) a formulation selected form the group consisting of injectables, orals, creams, suppositories, and intrapulmonary delivery formulations, (d) a cosmetic, and (e) a pharmaceutically active compound extracted from a mammalian cell culture.

6. The method of testing of claim 4, wherein the exogenous PrP gene is from a cow.

7. A transgenic mouse, produced by the process comprising the steps of:
   ablating both alleles of an endogenous PrP gene of a mouse embryonic stem cell;
   introducing a transgene comprised of an exogenous non-mouse PrP gene into said stem cell, wherein the exogenous PrP gene is comprised of a PrP gene native to a genetically diverse test mammal;
   introducing said stem cell having an ablated endogenous PrP gene and said exogenous PrP transgene into a mouse embryo;
   introducing said mouse embryo into a female mouse host;
   allowing said mouse embryo to develop into a chimeric mouse;
   breeding said chimeric mouse to a non-transgenic mouse; and
   identifying a first transgenic mouse that is heterozygous for the ablation in the endogenous PrP gene and whose somatic and germ cells comprise a genome that has operatively inserted therein an exogenous non-mouse PrP gene;
   breeding said first transgenic mouse with another first transgenic mouse; and
   identifying a second transgenic mouse that is homozygous for the ablation of the endogenous PrP gene and further having an exogenous, non-mouse PrP gene in its genome;
   wherein the exogenous PrP gene is expressed in the transgenic mouse, and further wherein the transgenic mouse is susceptible to infection with prions which generally only infect a genetically diverse test mammal.

8. The mouse of claim 7, wherein the exogenous PrP gene is operatively linked to a promoter which enhances expression of the exogenous PrP gene.

9. The mouse of claim 7, wherein the exogenous PrP gene is a bovine PrP gene.

10. A method of determining the presence of infectious prions in a sample obtained from a bovine; comprising:
    obtaining sample tissue from a bovine to be tested;
    inoculating a transgenic mouse with the sample wherein the mouse comprises (a) a genome wherein both alleles of an endogenous PrP gene are ablated and (b) a transgene expressing an exogenous bovine PrP gene; and
    observing the mouse for symptoms of prion disease within 200 days of inoculation.

* * * * *